(12) United States Patent
Urmey

(10) Patent No.: US 7,282,033 B2
(45) Date of Patent: Oct. 16, 2007

(54) POSITIONING SYSTEM FOR A NERVE STIMULATOR NEEDLE

(76) Inventor: William F. Urmey, 1 Flint Ave., Larchmont, NY (US) 10538

( * ) Notice: Subject to any disclaimer, the term of this patent is extended or adjusted under 35 U.S.C. 154(b) by 712 days.

(21) Appl. No.: 10/654,386

(22) Filed: Sep. 3, 2003

(65) Prior Publication Data
US 2004/0059247 A1    Mar. 25, 2004

Related U.S. Application Data

(60) Provisional application No. 60/408,026, filed on Sep. 4, 2002.

(51) Int. Cl.
*A61B 5/05* (2006.01)
(52) U.S. Cl. ...................................... 600/554
(58) Field of Classification Search ................ 600/554
See application file for complete search history.

(56) References Cited

U.S. PATENT DOCUMENTS

| | | | |
|---|---|---|---|
| 4,788,985 A * | 12/1988 | Manning et al. | 600/572 |
| 4,940,060 A * | 7/1990 | Gu et al. | 600/548 |
| 5,007,902 A * | 4/1991 | Witt | 604/117 |
| 5,129,402 A * | 7/1992 | Koll et al. | 600/572 |
| 5,284,153 A | 2/1994 | Raymond et al. | |
| 5,327,902 A * | 7/1994 | Lemmen | 600/547 |
| 5,456,662 A * | 10/1995 | Edwards et al. | 604/22 |
| 5,830,151 A | 11/1998 | Hadzic et al. | |
| 5,853,373 A | 12/1998 | Griffith | |
| 5,885,219 A | 3/1999 | Nightengale | |
| 5,928,158 A * | 7/1999 | Aristides | 600/547 |
| 6,312,392 B1 | 11/2001 | Herzon | |
| 6,533,732 B1 | 3/2003 | Urmey | |
| 6,564,078 B1 * | 5/2003 | Marino et al. | 600/373 |

FOREIGN PATENT DOCUMENTS

| | | |
|---|---|---|
| EP | 0 759 307 A | 2/1997 |
| EP | 01 98 1706 | 8/2005 |
| GB | 2 115 700 A | 9/1983 |

* cited by examiner

*Primary Examiner*—Max F. Hindenburg
*Assistant Examiner*—H. Q. Nguyen
(74) *Attorney, Agent, or Firm*—Seth Natter; Natter & Natter

(57) ABSTRACT

A target nerve or nerve plexus registration point is located utilizing a nerve stimulator needle positioned in a bore of a carrier. The carrier is configured with an electrically non-conductive smooth curved surface at a distal end of the bore. The needle tip is fixed in an operative cutaneous electrode position and the smooth curved surface of the carrier is forced against and compresses the epidermis, corium and subcutaneous tissue and traverses cutaneous surfaces to locate a target nerve or nerve plexus without physical penetration by the needle tip. The needle is then inserted at the located point, with or without the needle path being guided by the bore. In another embodiment, a subcutaneous portion of carrier is introduced and is pivoted about its introduction point to locate the target nerve.

20 Claims, 4 Drawing Sheets

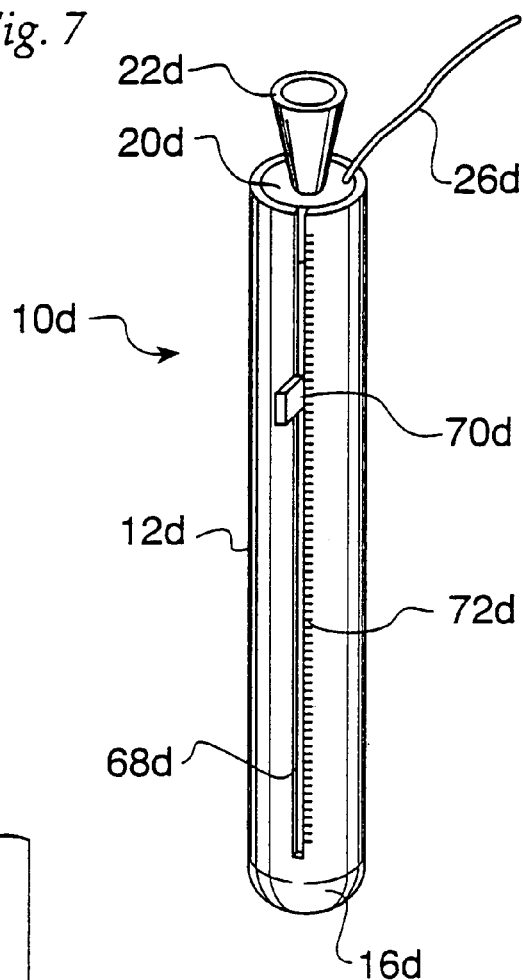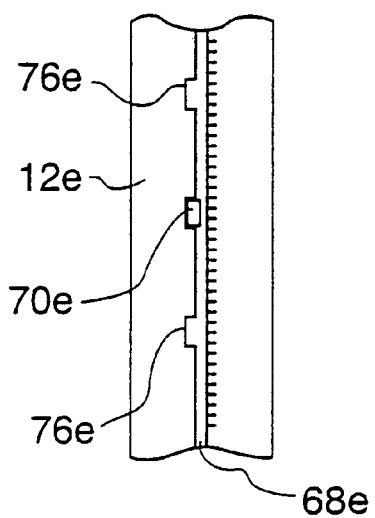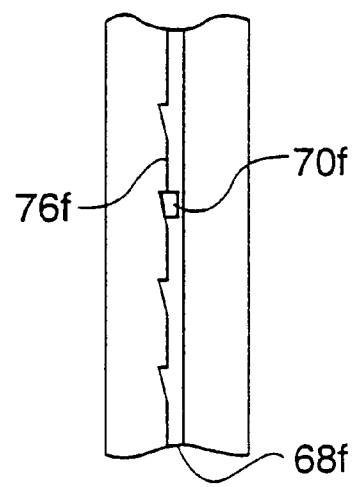

POSITIONING SYSTEM FOR A NERVE STIMULATOR NEEDLE

RELATED APPLICATIONS

This application claims the benefit of U.S. Provisional Application No. 60/408,026, filed Sep. 4, 2002.

BACKGROUND OF THE INVENTION

1. Field of the Invention

This invention relates generally to regional anesthesia and more particularly to a system for positioning a nerve stimulator needle in conjunction with various procedures, such as, the administration of an anesthetic blockade, neuro monitoring, electromyography and therapeutic intervention.

2. Antecedents of the Invention

The field of regional anesthesia relates to the practice of administering anesthesia to a specific body region during surgery, for the relief of postoperative pain, and for extended relief of trauma or chronic pain. Often, regional anesthesia has been found to be preferable to general anesthesia because of increased safety, the availability of postoperative pain control and decreased anesthetic costs.

Regional anesthesia delivery techniques strove to optimize administration of a local anesthetic in close proximity to a target or nerve plexus so as to establish a neural blockade. Successful administration of regional anesthesia was dependent upon the accurate placement of the anesthetic in relation to the target nerve or nerves.

Various techniques have been employed to assist in placement of an administration needle in close proximity to the target nerve, which was not externally visible. One of the traditional methods of needle placement involved eliciting paresthesia. Among the disadvantages of this technique was the lack of accurate patient responses amongst patients who were disoriented and/or sedated.

A prevalent technique employed the use of nerve stimulators electrically coupled to a nerve stimulator needle. Such method was premised upon the phenomenon that an electrical pulse is capable of stimulating a motor nerve fiber to contract an innervated muscle or cause paraesthesia, in the case of sensory nerve stimulation.

The nerve stimulator needle was placed within the tissue of the patient's body in the vicinity of the nerve to be blocked and then advanced until stimulation of the target nerve was achieved as determined by visually detecting muscle contractions or by eliciting a report that the patient felt the stimulus in response to the current flow through the stimulator needle.

The current supplied by the nerve stimulator was reduced as the nerve stimulator needle was further advanced, until stimulation of the target nerve was achieved using a reduced current level associated with a prescribed distance between the needle tip and the target nerve.

Thereafter, a portion of the anesthetic dose was administered through the needle to terminate the response to the nerve stimulation current. If the response was terminated by the initial administration, the needle was deemed to be properly positioned in proximity to the target nerve and the remaining dose of anesthetic was administered.

It should be understood, however, that the initial placement of the needle was dependent upon anatomic landmarks. Since anatomic landmarks varied from patient to patient, they constituted only an approximate starting zone or region to guide needle insertion. Successful administration was often dependent upon the skill and experience of the anesthesiologist. Multiple needle passes were required when the initial needle placement was not directly registered over the target nerve or nerve plexus or when the angle of introduction was anatomically incorrect.

Peripheral nerves have been stimulated with cutaneous electrodes at appropriate landmarks utilizing a coupling gel for monitoring the degree of neuromuscular blockade during general anesthesia when neuromuscular relaxing or paralyzing drugs were intravenously administered.

In U.S. Pat. No. 6,533,732, entitled: NERVE STIMULATOR NEEDLE GUIDANCE SYSTEM issued Mar. 18, 2003 to Applicant, there is disclosed a nerve stimulator needle guidance system having a cutaneous electrode with a conductive tip and a bore extending through the electrode. The electrode is coupled to a nerve stimulator to noninvasively locate a target nerve registration point while depressing the patient's dermal layers. Thereafter a nerve stimulator needle is introduced through the bore and into the patient at the located registration point. There is also disclosed, in Applicant's Application No. PCT/US01/32412, published Apr. 25, 2002, Publication No. 02/32289 82 a subcutaneous electrode guidance system for a nerve stimulator needle which utilized a smooth tipped electrode probe for locating the direction of a nerve or nerve plexus relative to a cutaneous introduction point.

SUMMARY OF THE INVENTION

A system for locating a target nerve or nerve plexus of a patient having cutaneous dermal layers including a corium includes a carrier having a shield with a smooth contour and an electrode having a tip selectively coupled to a current supply. The shield is electrically nonconductive and the tip has an operative position relative to the shield such that when the shield is pressed against the patient's dermal layers, the tip does not penetrate the patient's corium, while current flows from the tip through the patient for eliciting a neurologic response. When the shield is pressed against the patient's dermal layers and is moved laterally while maintaining pressure and current flow, the neurological response varies as a function of the position of the tip relative to the target nerve or nerve plexus.

In one embodiment, the tip of a nerve stimulator needle electrode is physically restrained against penetration through the corium while serving as a cutaneous electrode for locating a nerve or nerve plexus registration point. The needle is positioned within a bore of an electrically shielded nonconductive carrier having a smooth, blunt, shield at one end and is locked into a position such that the needle tip does not project beyond the shield a distance sufficient to penetrate the epidermis and corium while the carrier is depressed against and laterally displaced along dermal layers.

A set screw may be employed to bear against the needle shaft or hub for fixing the needle tip. Alternatively, a spring-loaded latch may bear against an indexing groove in the needle shaft or hub for fixing the needle tip. In a further embodiment, a snap fit engagement between the carrier and the nerve stimulator needle may be provided for fixing the needle tip.

The target nerve cutaneous registration point is located by applying a suitable current through the needle while depressing the patient's dermal layers with the shield and traversing a cutaneous zone until a suitable neuromuscular response is elicited. Thereafter the bore may be utilized as a guide for advancing the needle or the carrier may be removed, i.e.

separated from the needle, or positioned adjacent the proximal end of needle while the needle is advanced into the patient.

The needle shaft or hub may include a radial arm which is received in a vertical slot of the carrier for fixing the position of the needle tip and/or advancing the needle into the patient at the located registration point.

In a further embodiment, a subcutaneous guiding electrically shielded nonconductive carrier includes a smooth blunt end. The subcutaneous carrier is introduced through the skin utilizing a needle carried in a bore and projecting beyond the blunt end. The needle is then retracted so that the tip is flush or slightly recessed from the blunt end.

The blunt end is advanced to a desired depth beneath the skin fixed by a smooth lateral stop surface and the carrier is manipulated in a sweep pattern while the needle tip is maintained flush with or recessed from the contour of the blunt end. Nerve stimulation current is applied to the needle tip during manipulation to locate the direction of the target nerve relative to the introduction point. Axial pressure may be applied through the surface of the stop to compress the surrounding dermal layers during manipulation of the carrier.

After the direction of the target nerve is located, the position of the carrier is fixed and the nerve stimulator needle is advanced through the bore and beyond the blunt end, while applying a reduced level of current. When appropriate muscle contractions are elicited at low current levels, the nerve stimulator needle has been properly positioned for administration of anesthesia.

From the foregoing compendium, it will be appreciated that it is an aspect of the present invention to provide a positioning system for a nerve stimulator needle of the general character described which is not subject to the disadvantages of the antecedents of the invention.

It is a feature of the present invention to provide a positioning system for a nerve stimulator needle of the general character described, which simplifies the administration of neural blockade anesthesia.

Another aspect of the present invention is to provide a positioning system for a nerve stimulator needle of the general character described which utilizes a tip of a nerve stimulator needle to noninvasively locate a cutaneous entry point for the needle.

An additional feature of the present invention is to provide a positioning system for a nerve stimulator needle of the general character described with simplified electrical connection to a nerve stimulator current generator for both locating a cutaneous registration point of a target nerve and for advancement of a nerve stimulator needle toward the target nerve.

To provide a positioning system for a nerve stimulator needle of the general character described which is well suited for the introduction of a catheter for continuous regional anesthesia or analgesia is a further consideration of the present invention.

Another aspect of the present invention is to provide a cutaneous electrode which does not require the use of a coupling gel.

A still further feature of the present invention is to noninvasively employ a needle electrode on cutaneous surfaces in conjunction with a medical procedure.

An additional consideration of the present invention is to provide a positioning system for a nerve stimulator needle of the general character described which increases the efficiency of the administration of regional anesthesia.

To provide a positioning system for a nerve stimulator needle of the general character described which utilizes conventional nerve stimulators is yet a further aspect of the present invention.

Other aspects, features and considerations of the present invention in part will be obvious and in part will be pointed out hereinafter.

With these ends in view, the invention finds embodiment in certain combinations of elements, arrangements of parts and series of steps by which the aforesaid aspects, features and considerations and certain other aspects, features and considerations are attained, all with reference to the accompanying drawings and the scope of which will be more particularly pointed out and indicated in the appended claims.

BRIEF DESCRIPTION OF THE DRAWINGS

In the accompanying drawings in which are shown some of the various exemplary embodiments of the invention:

FIG. 7 is a perspective illustration a further alternate embodiment, wherein the carrier includes an enlarged bore extending from a proximal end and with a needle hub seated in the bore and with a radial arm projecting from the needle shaft.

FIG. 9 is an enlarged scale front elevational view of an alternate embodiment of the positioning system illustrated in FIG. 7 wherein the radial arm is selectively seated in a notch for fixing the position of the needle tip, FIG. 10 is a fragmentary large scale front elevational view similar to that of FIG. 9 illustrating a further embodiment wherein the radial arm is seated in a toothed notch for fixing the position of the needle tip.

DESCRIPTION OF THE PREFERRED EMBODIMENTS

Figure 1:
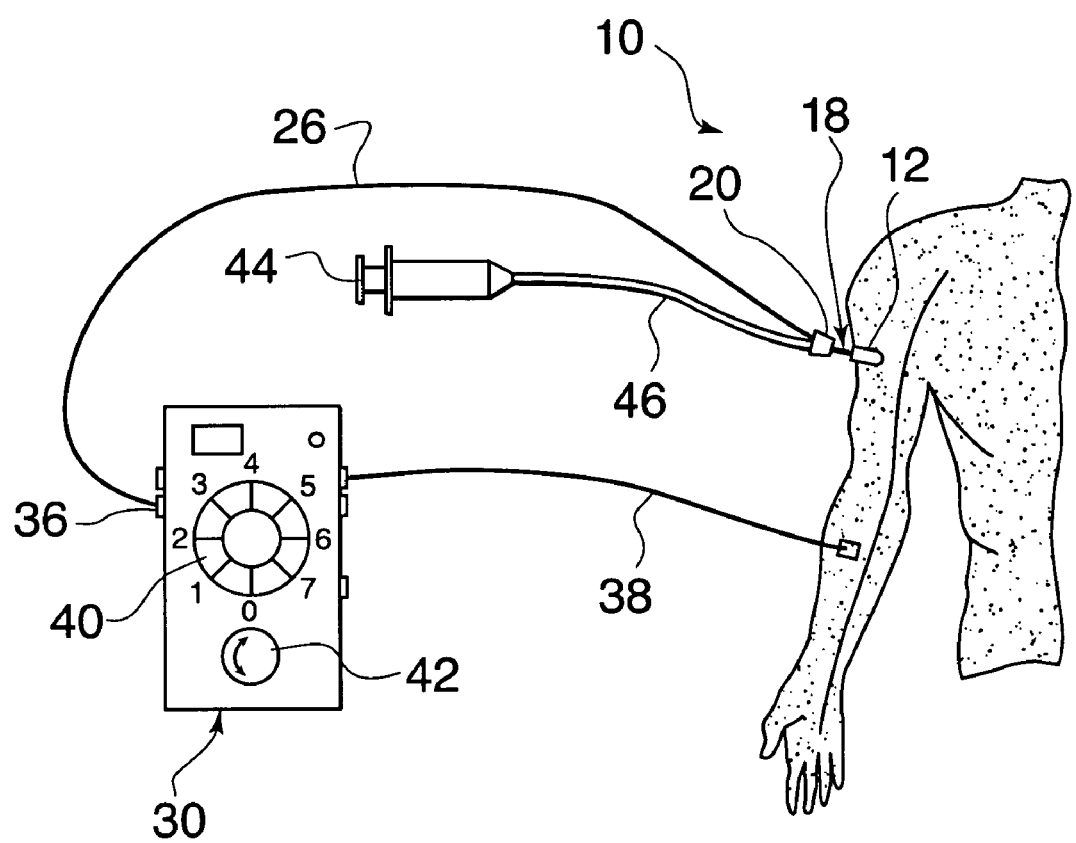
FIG. 1 is a schematized illustration of a positioning system for a nerve stimulator needle constructed in accordance with and embodying the invention as may be typically employed to locate a target median nerve and illustrating a nerve stimulator needle positioned within the bore of a carrier, with the needle being coupled to a nerve stimulator.

With reference now in detail to the drawings, wherein like numerals denote like components throughout the various figures, the reference numeral 10 denotes generally a positioning system for a nerve stimulator needle constructed in accordance with and embodying the invention.

Figure 2:
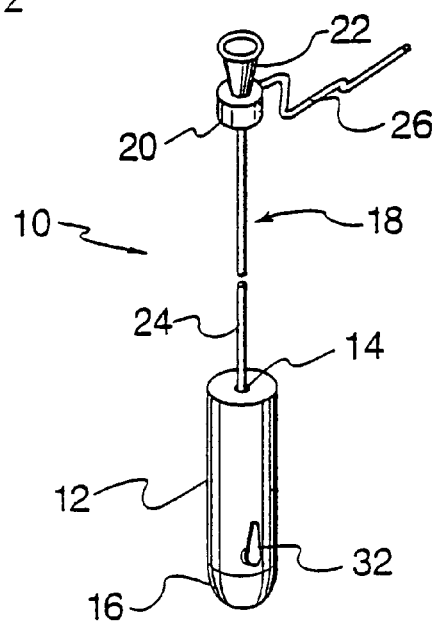
FIG. 2 is a perspective view of the positioning system illustrating a cylindrical carrier having an axial bore and a smooth blunt shield at one end and with the needle fixedly positioned within the bore such that the needle tip is substantially flush with the contour of the shield.

The positioning system 10 includes a carrier 12, illustrated in FIG. 2 as having a cylindrical body with an axial bore 14 extending therethrough. The carrier is formed of a material which is not electrically conductive, e.g. a thermoplastic. The most distal end of the carrier comprises a blunt, continuous, smooth, rounded, shield 16 which may be of hemispherical shape. A conventional nerve stimulator needle 18 includes a hub 20 at its proximal end from which extends a conventional Luer fining 22. A hollow needle shaft 24 extends axially from the hub 20 and an electrical lead 26 interconnects a sharp tip 28 of the needle shaft with a conventional nerve stimulator 30 illustrated in FIG. 1.

In accordance with the invention, there is provided a locking mechanism for engaging the needle shaft to temporarily lock the needle shaft 24 in an operative cutaneous electrode position wherein the needle tip 28 is flush with, slightly recessed from, or does not project beyond the contour of the shield 16 a distance sufficient to invasively penetrate into dermal layers, when the shield 16 is depressed against the dermal layers and laterally moved to locate a target nerve while in electrical contact with the dermal layers as will be explained in detail hereinafter.

Figure 3:
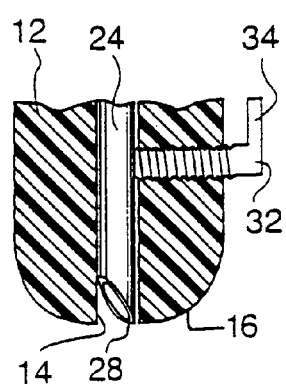
FIG. 3 is an enlarged scale sectional view through the carrier and illustrating a set screw which bears against the needle shaft for maintaining the needle tip in position.

As illustrated in FIG. 3, a set screw 32 having an actuating arm 34 may be threadably seated in a transverse bore of the carrier and may be engaged to bear down, i.e. apply lateral compressive force, against the needle shaft 24 to fix it in position.

With reference to FIG. 1, the nerve stimulator 30 includes known pulse generating and adjustable current control circuits, with an output terminal 36 connected to the electrical lead 26. There is additionally provided an output terminal coupled to a ground lead 38. The nerve stimulator 30 also includes conventional output current controls 40, 42.

As explained in detail in U.S. Pat. No. 6,533,732 and published application—PCT/US01/32412 both of which are both of which are incorporated herein by reference, for each of the various target nerves, optimal initial (cutaneous) or base level current flow values are provided.

Pursuant to the invention, the shield 16 of the carrier 12 is forced against, compresses and indents the patient's dermal layers, i.e. epidermis, corium and subcutaneous tissue, in an anatomic cutaneous zone consistent with the target nerve or nerve plexus. With the dermal layers and subcutaneous tissue indented, the needle tip is brought closer to the target nerve, thus facilitating transcutaneous stimulation to locate the nerve. The carrier then moves the needle tip across the cutaneous zone while pressure is maintained with current being transmitted through dermal layers and without the requirement for utilizing a coupling gel. A cutaneous registration point is located when it is determined that appropriate muscle contractions have been elicited with minimum current.

Thereafter the set screw 32 may be released and the needle shaft 24 is urged through the carrier bore 14 and into the patient, utilizing the carrier bore 14 as a guide and with reduced current flow from the current generator. Maintenance of the compressive force on the dermal layers and underlying tissue serves to fix the position of the target nerve while the needle is being advanced.

When nerve stimulation is achieved utilizing a reduced current level associated with the prescribed distance between the needle tip 28 and the target nerve, a portion of the anesthetic dose is administered from a syringe 44 through flexible tubing 46 which is connected to the Luer fitting 22. If the response terminates with the initial administration, the needle is deemed to be properly positioned for the procedure.

Upon completion of the procedure and removal of the needle shaft from the patient, it is preferable to withdraw the needle shaft into the bore 14 until the needle tip 28 is recessed within the bore to prevent inadvertent needle sticks. The used needle may be locked in such safety position utilizing the set screw 32 and thereafter the needle may be discarded in an appropriate manner.

It should also be appreciated that the positioning system of the present invention is readily adapted for determining a cutaneous registration point with the needle 18 thereafter inserted at the located point without utilizing the bore 14 as a guide. In such instance, after releasing the set screw 32, the carrier 12 is slid up the needle shaft to the proximal (hub) end and fixed in such position. The anesthesiologist is then free to insert the needle to locate the target nerve in a conventional manner.

Figure 4:
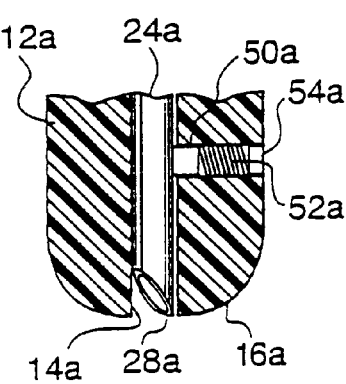
FIG. 4 is an enlarged scale sectional view through a modified carrier illustrating a spring biased pin which bears against the needle shaft to fix the position of the needle.

In FIG. 4 there is disclosed an alternate embodiment of the positioning system wherein like reference numerals have been employed to denote like components, however, bearing the suffix "a". In this embodiment, an alternate mechanism is employed for maintaining a tip 28a of a needle shaft 24a within a bore 14a of a carrier 12a in a position for noninvasive electrical contact with dermal layers as described with reference to the preceding embodiment.

A transverse radial bore of the carrier 12a intersects the bore 14a and carries a pin 50a which bears against the needle shaft 24a. A compression spring 52a is carried within the transverse bore between the pin 50a and an external plug 54a.

Figure 5:
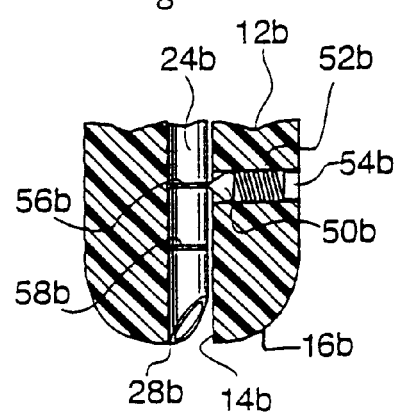
FIG. 5 is an enlarged scale sectional view through the carrier and illustrating a further embodiment wherein a spring biased latch engages a groove formed in the needle shaft to fix the position of the needle.

In FIG. 5 a further embodiment of the invention is illustrated wherein like numerals are employed to denote like components of the prior embodiments, however, bearing the suffix "b". In this embodiment, a transverse radial bore of a carrier 12b includes a latch pin 50b which is urged against a needle shaft 24b by a spring 52b, with the spring being carried in the transverse bore between the pin 50b and a plug 54b.

The pin 50b engages a groove 56b of the shaft 24b for fixing a position of a needle tip 28b in an operative cutaneous electrode position, i.e. slightly recessed from, flush with or which does not extend beyond the contour of a shield 16b so as to penetrate, but is in electrical contact with the dermal layers. A further groove 58b is provided in the needle shaft 24b in order to secure the needle tip within a bore 14b after the procedure has been completed, so as to avoid inadvertent needle sticks. An additional groove (not shown) may be provided to fix the carrier along the needle shaft 24b at a position adjacent the needle hub, which would enable a practitioner to advance the needle into the patient at the located point in a conventional manner, i.e. without utilizing the bore 14b as a guide.

Figure 6:
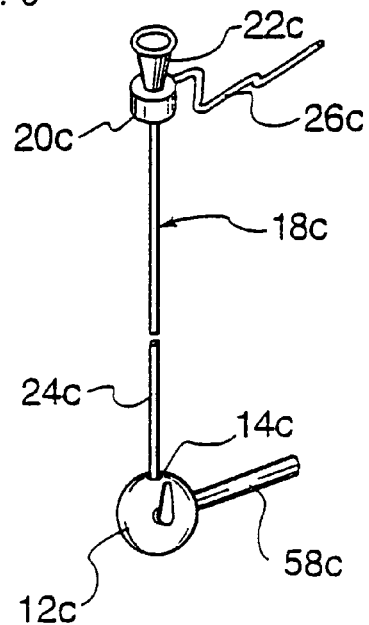
FIG. 6 is a perspective view of an alternate embodiment of the positioning system wherein the carrier is spherically shaped and includes a manipulating handle.

In FIG. 6 there is illustrated a further embodiment of the invention wherein like numerals have been employed to denote like components, however bearing the suffix "c". In this embodiment, a spherical carrier 12c having a bore 14c is employed. An integral manipulating handle 58c projects from the surface of the carrier 12c. The handle 58c is employed to both exert pressure for compressing dermal layers and underlying tissue as well as for movement of the carrier 12c along cutaneous surfaces.

Figure 8:
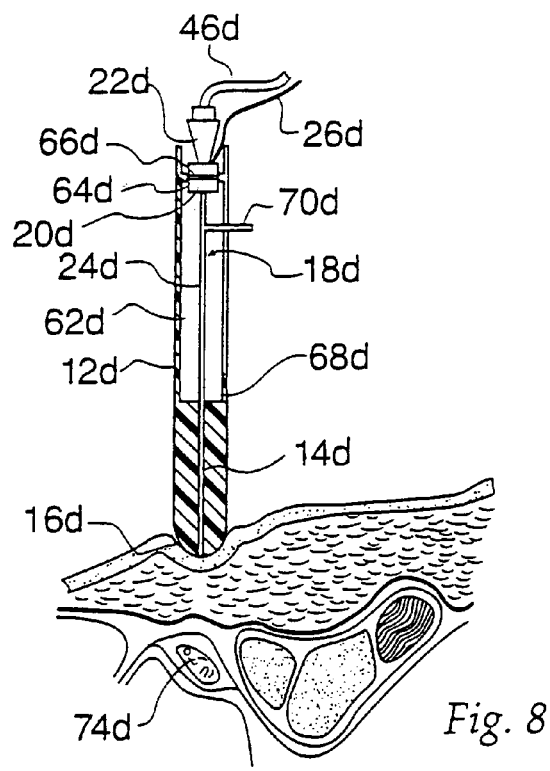
FIG. 8 is a sectional view through the positioning system illustrated in FIG. 7 and illustrating the technique of employing the positioning system for locating a femoral nerve.
Figure 11:
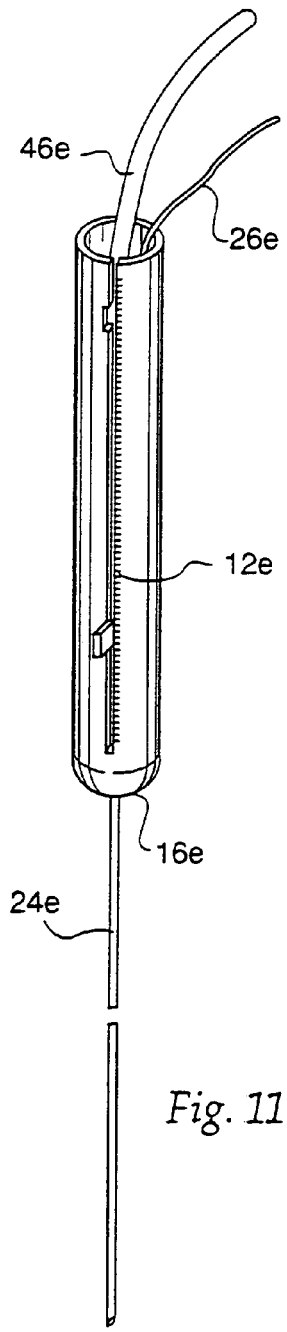
FIG. 11 is a perspective illustration of the FIG. 9 embodiment configured for conventional needle insertion after a cutaneous registration point has been located.

In another embodiment of the positioning system illustrated in FIG. 7 and FIG. 8, like numerals have been employed to denote like components, however bearing the suffix "d". In this embodiment, an elongated cylindrical carrier 12d includes an enlarged proximal bore 62d having a diameter sufficient to accommodate a hub 20d as well as a Luer fitting 22d of a needle 18d. Adjacent the distal end of the carrier 12d, a coaxial bore 14d is provided for accommodating a needle shaft 24d. Connected to the needle shaft 24d through the hub 20d is a nerve stimulator electrical lead 26d and a length of tubing 46d interconnects the Luer fitting 22d with a syringe.

The tip of the needle 18d is maintained in operative cutaneous electrode position by an annular integral rib 64d, formed on the interior surface of the bore 62d adjacent its proximal end. The rib 64d is in snap fit engagement with an annular groove 66d formed in the hub 20d.

It should be noted that the carrier 12d includes a longitudinal slot 68d and a radial arm 70d extends from the needle shaft 24d through the slot. The arm 70d may be manipulated axially to urge the needle 18d into the patient at the located registration point. Indexing marks 72d are optionally provided along the slot 68d to gauge the depth of penetration. FIG. 8 illustrates the positioning system in use for locating a point in registration with a target femoral nerve 74d.

In FIG. 9 there is shown a variation of the embodiment of FIG. 7 and FIG. 8 wherein one longitudinal edge of a slot 68e includes spaced notches or indentations 76e, with a radial arm 70e projecting from a needle shaft being rotated from the slot 68e and seated in a selected notch to fix the position of the needle shaft. The selected notch may be one for positioning the tip of the needle in operative cutaneous electrode position or for safely receiving the tip of the needle within the carrier after the needle is withdrawn from the patient. In FIG. 9, the arm 70e is seated in a notch position wherein the major portion of a needle shaft 24e is accessible for insertion into the patient at the located registration point without utilizing the needle receiving bore of the carrier 12e as a guide.

In a still further modification is illustrated in FIG. 10, wherein a plurality of angular notches 76f are provided along an edge of a slot 68f and a portion of a radial arm 70f is angularly configured for locking engagement with a desired notch to facilitate advancement of the needle shaft and retard retraction into the carrier.

Figure 12:
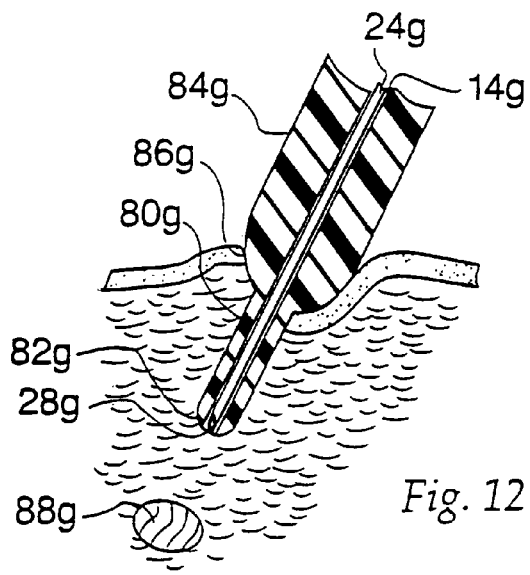
FIG. 12 is a sectional view through a further embodiment of the invention including a subcutaneous carrier having an enlarged grip which is employed for depressing dermal layers while manipulating the carrier to locate the direction of a target nerve.

With reference now to FIG. 12 wherein a further embodiment of the invention is illustrated, like numerals have been employed to denote like components of the prior embodiments, however bearing the suffix "g".

A relatively small diameter generally cylindrical subcutaneous guiding carrier 80g includes a smooth distal end 82g and a large diameter concentric proximal gripping portion 84g. The gripping portion 84g is interconnected to the subcutaneous guiding carrier 80g at a curved step 86g which provides a depth of penetration stop as will be pointed out hereinafter. A bore 14g, dimensioned to receive a needle shaft 24g, extends concentrically through the subcutaneous guiding carrier 80g and the grip 84g.

The subcutaneous guiding carrier 80g is introduced through the dermal layers at a penetration point utilizing a needle tip 28g with the needle shaft 24g being positioned to extend the tip 28g beyond the smooth distal end 82g. The needle shaft 24g is then withdrawn into the bore 14g until the needle tip 28g is flush with or slightly recessed from the distal end 82g.

After the subcutaneous guiding carrier 80g reaches a desired depth of penetration which is fixed by the step 86g, the guiding carrier 80g is manipulated in a sweep pattern, while nerve stimulation current is applied. The smooth distal end 82g of the subcutaneous carrier 80g reduces the trauma which would otherwise result if an exposed needle tip were manipulated in the sweep pattern.

Having thus described the invention there is claimed as new and desired to be secured by Letters Patent:

1. A positioning system for cutaneously and noninvasively locating a target nerve or nerve plexus of a subject for the administration of regional anesthesia at the target nerve or nerve plexus, the system comprising a carrier, a bore extending through the carrier, the bore having a proximal end and a most distal end, the carrier having a surface with a continuous smooth contour extending laterally at the most distal end of the bore, the surface being electrically nonconductive, a nerve stimulator needle having a hollow shaft for delivery of regional anesthesia, the needle being carried in the bore, the needle having a sharp tip, the needle tip being at the most distal end of the bore in an operative cutaneous electrode position such that when the surface is pressed against dermal layers of the subject, the sharp tip contacts the dermal layers without invasive penetration, the needle tip being selectively coupled to a current supply for eliciting a neurological response to current flow, the needle tip being locked against movement relative to the carrier when in the operative cutaneous electrode position, whereby transcutaneous current flow from the tip through the subject is assured when the surface is pressed against dermal layers of the subject without invasive penetration of the tip for locating a dermal position proximate the target nerve or nerve plexus and the needle thereafter advanced at the located position beyond the distal end of the bore, through dermal layers and into the subject for subcutaneous location of the target nerve or nerve plexus for the administration of regional anesthesia.

2. A positioning system as constructed in accordance with claim 1 further including a locking mechanism comprising a portion of the carrier in engagement with the needle to releasably lock the needle tip relative to the carrier when in the operative cutaneous electrode position.

3. A positioning system as constructed in accordance with claim 2 wherein the needle shaft includes a groove which is engaged by a portion of the carrier to releasably lock the needle tip relative to the carrier when in the operative cutaneous electrode position.

4. A positioning system as constructed in accordance with claim 2 wherein the needle includes a hub, a portion of the carrier engaging the hub to releasably lock the needle tip relative to the carrier when in the operative cutaneous electrode position.

5. A positioning system as constructed in accordance with claim 2 wherein the portion of the carrier applies a lateral compressive force against the needle.

6. A positioning system as constructed in accordance with claim 2 wherein the portion of the carrier in engagement with the needle comprises a pin.

7. A positioning system as constructed in accordance with claim 1 wherein the carrier includes an axial slot extending from the bore and the needle includes a radial arm, the slot including at least one notch formed along a longitudinal edge of the slot, the notch being dimensioned to receive the radial arm to releasably lock the needle tip in the operative cutaneous electrode position.

8. A positioning system as constructed in accordance with claim 1 wherein the bore comprises a first bore, the carrier having a second bore, the first bore and the second bore being coaxial, the second bore extending from the proximal end of the first bore, the needle including a proximal end and a distal end, the tip being positioned at the distal end of the needle and a hub being positioned at the proximal end of the needle, the second bore being dimensioned to receive the hub.

9. A positioning system as constructed in accordance with claim 1 wherein the carrier includes an axial slot extending from the bore and the needle includes a radial arm received in the slot, whereby the radial arm may be employed for advancing the needle tip into the subject after the target nerve or nerve plexus has been located and the needle tip is unlocked.

10. A positioning system for noninvasively locating a target nerve or nerve plexus of a subject for the administration of regional anesthesia, the system comprising a carrier, a bore extending through the carrier, the bore having a proximal end and a most distal end, the carrier having a curved surface with a smooth continuous contour at the most distal end of the bore, the surface being electrically nonconductive, a needle having a hollow shaft for delivery of regional anesthesia, the needle being carried in the bore, the needle having a sharp tip, the sharp tip being selectively coupled to a current supply, the needle being releasably locked in an operative position within the bore with the sharp tip at the most distal end of the bore to prevent invasive penetration of the needle into the subject while assuring current flow from the tip and through the subject for eliciting a neurological response which varies as a function of the position of the surface relative to the target nerve or nerve plexus, whereby the needle thereafter unlocked and thereafter advanced invasively beyond the most distal end and toward a target nerve or nerve plexus when the neurological response indicates that the surface is proximate the target nerve or nerve plexus.

11. A positioning system for cutaneously and noninvasively locating a target nerve or nerve plexus of a subject for the administration of regional anesthesia, the subject having cutaneous dermal layers including a corium, the system comprising a carrier, the carrier having a continuous smooth blunt shield at a most distal end of the carrier, the shield being electrically nonconductive, a hollow nerve stimulator needle electrode including a sharp tip, the electrode being releasably locked in an operative position relative to the carrier with the sharp tip at and not projecting beyond the shield, the sharp tip being selectively coupled to a current supply for eliciting a neurological response to current flow, the operative position being such that when the shield is pressed against the dermal layers, the sharp tip contacts the dermal layers without invasive penetration of the corium, whereby when a neurological response indicative of proximity to the target nerve is observed, the needle is thereafter unlocked and advanced through the corium and toward a target nerve or nerve plexus.

12. A noninvasive positioning system for the administration of regional anesthesia in locating a target nerve or nerve plexus of a subject having cutaneous dermal layers including a corium, the system comprising a carrier having a bore, the carrier having a shield with a continuous smooth contour at a most distal end of the bore, the shield being electrically nonconductive, a hollow electrode, the electrode having a sharp tip, the sharp tip being in an operative position at the most distal end of the bore and being selectively coupled to a current supply, the electrode being releasably locked in the operative position with the sharp tip at the most distal end of the bore, whereby when the shield is pressed against the dermal layers, the sharp tip contacts the dermal layers without invasive penetration of the corium and when current is supplied to the tip, current flows through the subject for eliciting a neurological response which varies as a function of the lateral position of the tip on the dermal layers relative to the target nerve or nerve plexus.

13. A positioning system as constructed in accordance with claim 12 wherein the contour is curved.

14. A positioning system as constructed in accordance with claim 13 wherein the contour is hemispherical.

15. A positioning system as constructed in accordance with claim 1 wherein the contour is curved.

16. A positioning system as constructed in accordance with claim 15 wherein the contour is hemispherical.

17. A positioning system as constructed in accordance with claim 1 wherein the current supply comprises a nerve stimulator.

18. A positioning system as constructed in accordance with claim 10 wherein the contour is hemispherical.

19. A positioning system as constructed in accordance with claim 11 wherein the shield is hemispherical.

20. A positioning system as constructed in accordance with claim 10 wherein a portion of the carrier is in engagement with the needle to releasably lock the needle in the operative position.

* * * * *